United States Patent [19]
Fisher et al.

[11] Patent Number: 5,626,023
[45] Date of Patent: May 6, 1997

[54] CRYOGENIC RECTIFICATION SYSTEM FOR FLUORINE COMPOUND RECOVERY USING ADDITIVE LIQUID

[75] Inventors: Theodore F. Fisher, Amherst; Yijian Jin, Tonawanda, both of N.Y.

[73] Assignee: Praxair Technology, Inc., Danbury, Conn.

[21] Appl. No.: 389,480

[22] Filed: Feb. 16, 1995

[51] Int. Cl.$^6$ .................................................. F25J 3/00
[52] U.S. Cl. .................................................. 62/625; 62/918
[58] Field of Search .................................................. 62/17, 20

[56] References Cited

U.S. PATENT DOCUMENTS

| | | | |
|---|---|---|---|
| 3,282,801 | 11/1966 | Wüst et al. | 62/20 |
| 3,998,180 | 12/1976 | Hawkins et al. | 118/5 |
| 4,038,332 | 7/1977 | Carter | 62/20 |
| 4,081,574 | 3/1978 | Hawkins et al. | 427/237 |
| 4,484,954 | 11/1984 | Tarancon | 148/6.3 |
| 5,201,918 | 4/1993 | Vobach | 62/20 |
| 5,367,881 | 11/1994 | Henzler | 62/11 |

*Primary Examiner*—Ronald C. Capossela
*Attorney, Agent, or Firm*—Stanley Ktorides

[57] ABSTRACT

A cryogenic system for the recovery of fluorine compounds from a carrier gas stream such as an effluent stream from a semiconductor facility comprising combining the carrier gas feed stream with additive liquid to keep fluorine compounds from solidifying and to reduce the vapor pressure of the fluorine compounds, followed by separation and recovery using a cryogenic rectification column system.

20 Claims, 3 Drawing Sheets

CRYOGENIC RECTIFICATION SYSTEM FOR FLUORINE COMPOUND RECOVERY USING ADDITIVE LIQUID

TECHNICAL FIELD

This invention relates to the separation and recovery of fluorine compounds from a fluorine compound-containing stream. It is particularly useful for recovering fluorine compounds from an effluent of a semiconductor production facility.

BACKGROUND ART

Fluorine compounds are used in many manufacturing processes. In particular, they are widely used in the manufacture of semiconductors. Fluorine compounds are among the more costly of the more commonly used chemicals in manufacturing processes and, moreover, are among the more environmentally detrimental of such chemicals. Accordingly there is a need for recovering fluorine compounds used in manufacturing processes so that they not cause environmental problems and also so that they may be reused.

One method currently used by industry for ensuring that fluorine compounds are not released to the environment involves combustion of the fluorine compounds contained in an effluent stream. While this method effectively destroys the fluorine compounds thus preventing environmental pollution, it also makes it impossible to reuse the fluorine compounds. This method is also disadvantageous because it generates waste gases such as hydrogen fluoride and nitrogen oxides which require further treatment. Furthermore, combustion processes require fuel and oxidant to operate, adding further operating and capital costs to the manufacturing operation.

Another method currently used by industry for the recovery of fluorine compounds is adsorption wherein the fluorine compounds are adsorbed onto adsorbent under elevated pressure and desorbed from the adsorbent under vacuum. This method is disadvantageous because very high power consumption is needed to carry out the requisite pressurization and depressurization. Moreover, the fluorine compound mixture from the desorption generally requires further purification before the components of the mixture can be reused. Still further, adsorption processes do not have the flexibility to deal with the dramatic changes in fluorine compound concentrations and flow rates which characterize manufacturing effluent streams such as those from a semiconductor manufacturing plant.

Accordingly it is an object of this invention to provide an improved fluorine compound recovery system.

It is another object of this invention to provide an improved fluorine compound recovery system which does not generate significant amounts of waste gas.

It is a further object of this invention to provide a fluorine compound recovery system which can produce fluorine compound product without need for significant further separation or purification for reuse.

It is yet another object of this invention to provide a fluorine compound recovery system which can operate effectively in spite of large changes in fluorine compound concentrations and flow rates in the stream to be treated.

SUMMARY OF THE INVENTION

The above and other objects which will become apparent to those skilled in the art upon a reading of this disclosure are attained by the present invention one aspect of which is:

A method for recovering fluorine compounds comprising:

(A) combining a gaseous feed comprising carrier gas and fluorine compounds with additive liquid to form a mixed stream;

(B) partially condensing the mixed stream to produce vapor comprising carrier gas and fluorine compound-containing additive liquid;

(C) passing the fluorine compound-containing additive liquid into a rectification column as column feed and separating the column feed within said rectification column by cryogenic rectification into fluorine compound-containing top vapor and bottom additive liquid; and (D) withdrawing fluorine compound-containing top vapor from the rectification column and recovering at least a portion thereof as product fluorine compounds.

Another aspect of the invention is:

Apparatus for the recovery of fluorine compounds comprising:

(A) means for combining additive liquid with gaseous feed comprising fluorine compounds to produce a mixed stream;

(B) a heat exchanger and means for passing the mixed stream through the heat exchanger;

(C) a rectification column and means for passing liquid from the heat exchanger into the rectification column; and (D) means for recovering fluorine compounds taken from the upper portion of the rectification column.

Yet another aspect of the invention is:

A method for recovering fluorine compounds comprising:

(A) combining a gaseous feed comprising carrier gas, high volatility fluorine compounds and low volatility fluorine compounds with additive liquid to form a mixed stream;

(B) partially condensing the mixed stream to produce vapor comprising carrier gas and additive liquid comprising high volatility and low volatility fluorine compounds;

(C) passing the additive liquid comprising high volatility and low volatility fluorine compounds into a first rectification column as first column feed and separating the first column feed within said first rectification column by cryogenic rectification into top vapor comprising high volatility fluorine compounds and additive liquid comprising low volatility fluorine compounds;

(D) withdrawing top vapor comprising high volatility fluorine compounds from the first rectification column and recovering at least a portion thereof as product fluorine compounds;

(E) passing additive liquid comprising low volatility fluorine compounds into a second rectification column as second column feed and separating the second column feed within said second rectification column by cryogenic rectification into top vapor comprising low volatility fluorine compounds and residual additive liquid; and (F) withdrawing top vapor comprising low volatility fluorine compounds from the second rectification column and recovering at least a portion thereof as product fluorine compounds.

A further aspect of the invention is:

Apparatus for the recovery of fluorine compounds comprising:

(A) means for combining additive liquid with gaseous feed comprising fluorine compounds to produce a mixed stream;

(B) a heat exchanger and means for passing the mixed stream through the heat exchanger;

(C) a first rectification column and means for passing liquid from the heat exchanger into the first rectification column;

(D) means for recovering fluorine compounds taken from the upper portion of the first rectification column;

(E) a second rectification column and means for passing liquid from the lower portion of the first rectification column into the second rectification column; and (F) means for recovering fluorine compounds taken from the upper portion of the second rectification column.

As used herein the term "fluorine compounds" means one or more compounds comprising fluorine.

As used herein the term "high volatility fluorine compounds" means one or more fluorine compounds having a normal, atmospheric pressure, boiling point below 150° K. Examples include carbon tetrafluoride ($CF_4$) and nitrogen trifluoride ($NF_3$).

As used herein the term "low volatility fluorine compounds" means one or more fluorine compounds which are not high volatility fluorine compounds. Examples include hexafluoroethane ($C_2F_6$), pentafluoroethane ($C_2HF_5$), fluoroform, ($CHF_3$), methyl fluoride ($CH_3F$) and sulfur hexafluoride ($SF_6$).

As used herein, the term "rectification column" means a distillation or fractionation column or zone, i.e., a contacting column or zone wherein liquid and vapor phases are countercurrently contacted to effect separation of a fluid mixture, as for example, by contacting of the vapor and liquid phases on a series of vertically spaced trays or plates mounted within the column and/or on packing elements such as structured or random packing. For a further discussion of rectification columns, see the Chemical Engineer's Handbook fifth edition, edited by R. H. Perry and C. H. Chilton, McGraw-Hill Book Company, New York, Section 13, *The Continuous Distillation Process*.

Vapor and liquid contacting separation processes depend on the difference in vapor pressures for the components. The high vapor pressure (or more volatile or low boiling) component will tend to concentrate in the vapor phase whereas the low vapor pressure (or less volatile or high boiling) component will tend to concentrate in the liquid phase. Partial condensation is the separation process whereby cooling of a vapor mixture can be used to concentrate the volatile component(s) in the vapor phase and thereby the less volatile component(s) in the liquid phase. Rectification, or continuous distillation, is the separation process that combines successive partial vaporizations and condensations as obtained by a countercurrent treatment of the vapor and liquid phases. The countercurrent contacting of the vapor and liquid phases is generally adiabatic and can include integral (stagewise) or differential (continuous) contact between the phases. Separation process arrangements that utilize the principles of rectification to separate mixtures are often interchangeably termed rectification columns, distillation columns, or fractionation columns. Cryogenic rectification is a rectification process carried out, at least in part, at temperatures at or below 150 degrees Kelvin (K).

As used herein, the term "indirect heat exchange" means the bringing of two fluid streams into heat exchange relation without any physical contact or intermixing of the fluids with each other.

As used herein the term "recovery as product" means removal from the system. Preferably fluorine compounds recovered by the practice of this invention are reused, either directly or after further processing.

As used herein the terms "upper portion" and "lower portion" of a column mean those sections of a column respectively above and below the midpoint of the column.

DETAILED DESCRIPTION

The invention will be described in detail with reference to the drawings.

Figure 1:
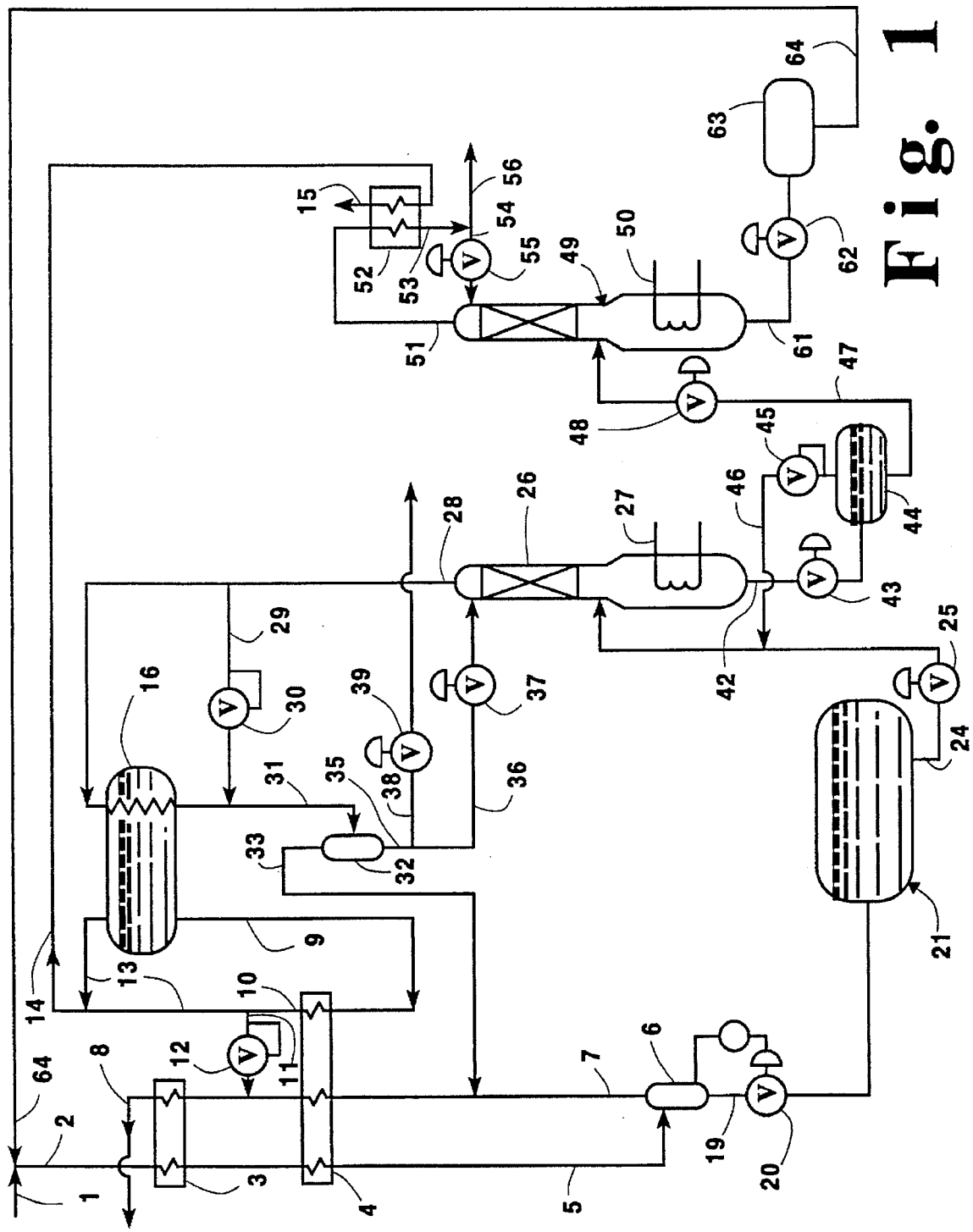
FIG. 1 is a schematic flow diagram of a preferred embodiment of the fluorine compound recovery system of this invention.

Referring now to FIG. 1, gaseous feed 1 which has been pressurized to a pressure of at least 18 and preferably 20 pounds per square inch absolute (psia) and has been treated to remove particulate and chemically active impurities such as hydrogen fluoride, carbon dioxide and water, and which comprises nitrogen carrier gas, high volatility fluorine compounds and low volatility fluorine compounds, is combined with additive liquid 64 to form mixed stream 2. The addition of the liquid to the gaseous feed, when the latter is at ambient temperature, will cause flash vaporization of the additive liquid, with the result that the mixed stream is an all vapor stream at a somewhat chilled temperature. If the gaseous feed was sufficiently precooled prior to being combined with the additive liquid, the mixed stream would be a two phased stream. The carrier gas of the gaseous feed may comprise other gases in addition to or in place of nitrogen such as oxygen, argon, helium and/or hydrogen.

The mixing of the additive liquid with the gaseous feed serves two purposes. The additive liquid acts as a solvent which prevents certain of the fluorine compounds from separating out of the condensed phase as solids during the subsequent cooling. In addition, the additive liquid lowers the concentration of the high volatility fluorine compounds in the condensed phase, resulting in a reduction in their concentrations in the equilibrium vapor phase which is separated and passed out of the system without being subject to recovery. The additive liquid has an atmospheric pressure freezing point lower than 100° K. and a vapor pressure less than 1.0 mmHg, preferably less than 0.01 mmHg, at 100° K. Perfluoropropane ($C_3F_8$) is the preferred additive liquid. Propane, ethane and mixtures thereof may also be used as the additive liquid.

Mixed stream 2 is then passed through at least one heat exchanger wherein it is cooled to a temperature within the range of from 90° to 130° K. such that the feed is partially condensed to produce vapor comprising carrier gas and additive liquid comprising high volatility and low volatility fluorine compounds. In the embodiment illustrated in FIG. 1 mixed stream 2 passes through two such heat exchangers 3 and 4.

Resulting stream 5 is then passed to phase separator 6 where it is separated into nitrogen-containing vapor and additive liquid comprising high volatility and low volatility fluorine compounds. The nitrogen-containing vapor is passed as stream 7 from phase separator 6 through heat exchangers 4 and 3 to carry out, by indirect heat exchange, the partial condensation of feed stream 2, and the resulting warmed nitrogen-containing vapor is removed from the system as stream 8.

The embodiment illustrated in FIG. 1 is a preferred embodiment wherein additional cryogenic liquid, e.g. liquid nitrogen, is used to carry out by indirect heat exchange the partial condensation of the feed. In this embodiment illustrated in FIG. 1, cryogenic liquid is passed from within tank 16 in line 9 through heat exchanger 4. Resulting stream 10 is then combined with stream 13 to form stream 11 which is passed through valve 12 into line 7 upstream of heat exchanger 3. Boil off vapor from tank 16 is passed out from tank 16 in stream 13 and a portion 14 is employed in a downstream part of the system.

Additive liquid comprising high volatility and low volatility fluorine compounds is withdrawn from phase separator 6 as stream 19 and preferably passed through valve 20 into first batch storage tank 21 where it is stored for subsequent batch-wise processing. The use of tank 21 is advantageous when there is a significant variance in the fluorine compound concentration in the gaseous feed and/or in the gaseous feed flow rate. Additive liquid comprising high volatility and low volatility fluorine compounds is passed from tank 21 in stream 24 through valve 25 as first column feed into the lower portion of first rectification column 26 which is driven by external heat input through heat input line 27.

The rectification steps may be operated in a batch mode. Within first rectification column 26 the first column feed is separated by cryogenic rectification into top vapor comprising high volatility fluorine compounds and additive liquid comprising low volatility fluorine compounds. It will be recognized by those skilled in the art that the top vapor from column 26 may initially contain some carrier gas which has been dissolved in stream 24 and may also contain some low volatility fluorine compounds. Similarly, the additive liquid from column 26 may contain some high volatility fluorine compounds.

Top vapor comprising high volatility fluorine compounds is withdrawn from the upper portion of first rectification column 26 as stream 28 and at least a portion thereof is recovered as product fluorine compounds. In the embodiment illustrated in FIG. 1, stream 28 is passed through tank 16 in indirect heat exchange with the liquid within tank 16 and is partially condensed. A portion 29 of stream 28 may be passed through valve 30 so as to bypass tank 16. Resulting partially condensed stream 31 is then passed into phase separator 32. Vapor, comprised primarily of carrier gas, is passed out from phase separator 32 in stream 33, and passed into stream 7 upstream of heat exchangers 4 and 3. Liquid is withdrawn from phase separator 32 as stream 35. A portion 36 of stream 35 is passed through valve 37 and into the upper portion of first rectification column 26 as reflux. After essentially all of the carrier gas has been exhausted from the first rectification column through stream 33, another portion 38 of stream 35 is passed through valve 39 and recovered as product fluorine compounds comprising primarily high volatility fluorine compounds.

Following removal of most of the high volatility fluorine compounds from column 26 through stream 38, additive liquid comprising low volatility fluorine compounds is withdrawn from the lower portion of first rectification column 26 as stream 42 and passed through valve 43 into second batch storage tank 44 where it is stored for subsequent batch-wise processing. The use of tank 44 is advantageous when there is a significant variance in the fluorine compound concentration in the gaseous feed and/or in the gaseous feed flow rate. Any liquid that is vaporized within tank 44 may be passed out from tank 44 through valve 45 in line 46 and combined with first column feed stream 24 and then into first rectification column 26. Additive liquid comprising low volatility fluorine compounds is passed from tank 44 in stream 47 through valve 48 as second column feed into the lower portion of second rectification column 49 which is driven by external heat input through heat input line 50.

Within second rectification column 49 the second column feed is separated by cryogenic rectification into top vapor comprising low volatility fluorine compounds and residual additive liquid. Top vapor comprising low volatility fluorine compounds is withdrawn from the upper portion of second rectification column 49 as stream 51 and at least a portion thereof is recovered as product fluorine compounds. In the embodiment illustrated in FIG. 1, stream 51 is condensed by passage through heat exchanger 52 in indirect heat exchange with stream 14 which is then passed out of the system as stream 15. Resulting stream 53 is withdrawn from heat exchanger 52 and a portion 54 is passed through valve 55 and into the upper portion of second rectification column 49 as reflux. Another portion 56 of stream 53 is recovered as product fluorine compounds. When more than one fluorine compound is to be recovered, each compound may be recovered sequentially.

Residual additive liquid is withdrawn from the lower portion of second rectification column 49 as stream 61 and passed through valve 62 into additive liquid storage tank 63. From tank 63 the residual additive liquid is withdrawn as stream 64 and combined with gaseous feed stream 1 to form mixed stream 2.

The embodiment of the invention illustrated in FIG. 1 is a preferred embodiment, in part, because it enables the separate recovery of high volatility fluorine compounds and low volatility fluorine compounds as the product fluorine compounds. When the incoming gaseous feed does not contain appreciable amounts of both high volatility and low volatility fluorine compounds, or when separate recovery of high volatility and low volatility fluorine compounds is not desired, the embodiment of the invention illustrated in FIG. 2 may be employed.

Figure 2:
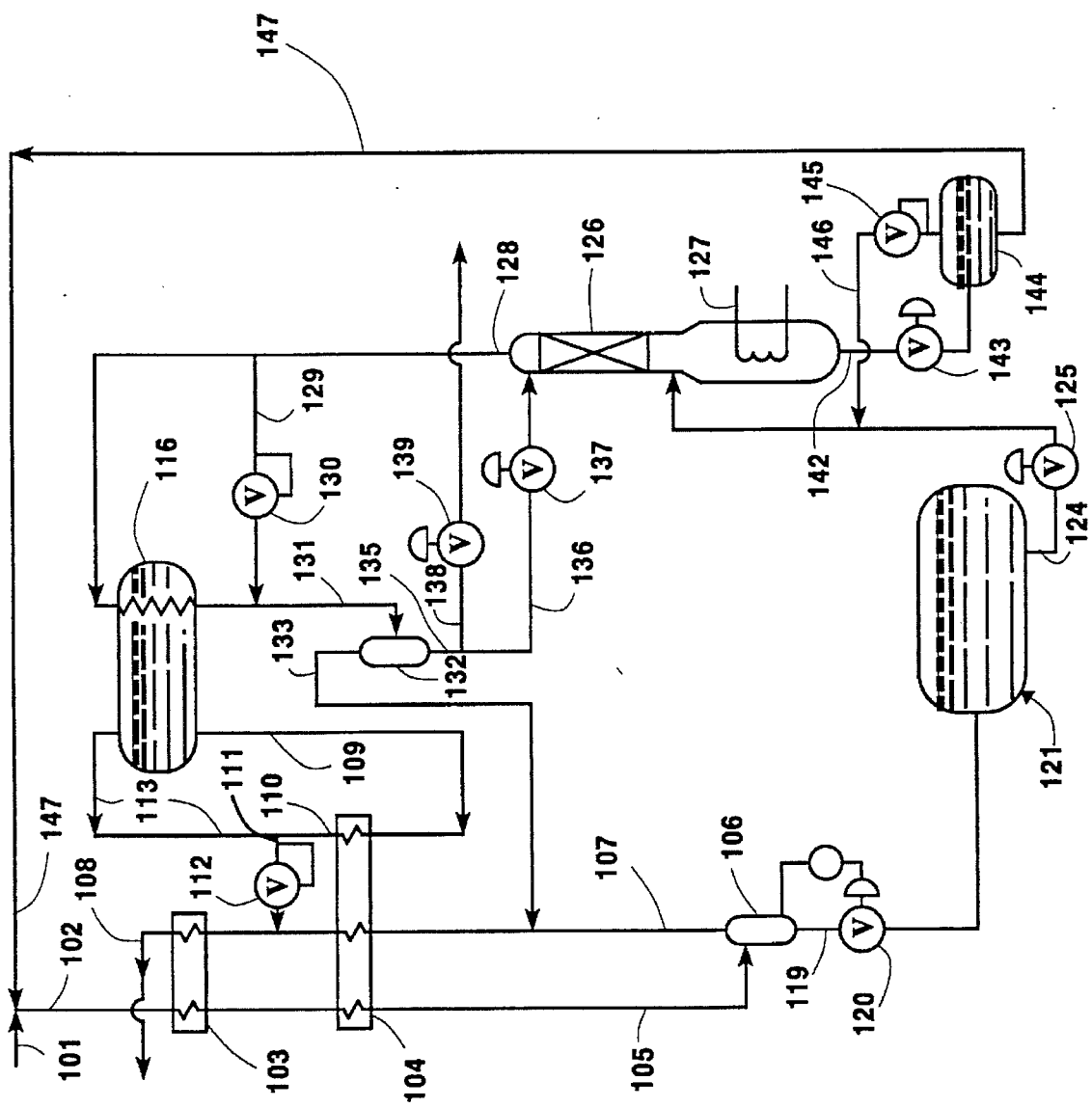
FIG. 2 is a schematic flow diagram of another embodiment of the fluorine compound recovery system of this invention.

Referring now to FIG. 2, gaseous feed 101 which has been pressurized to a pressure of at least 18 and preferably 20 psia and has been treated to remove particulate and chemically active impurities such as hydrogen fluoride, carbon dioxide and water, and which comprises nitrogen as the carrier gas and fluorine compounds, is combined with additive liquid 147 to form mixed stream 102. The carrier gas of the gaseous feed may comprise other gases in addition to or in place of nitrogen such as oxygen, argon, helium and/or hydrogen.

The mixing of the additive liquid with the gaseous feed serves two purposes. The additive liquid acts as a solvent which prevents certain of the fluorine compounds from separating out of the condensed phase as solids during the subsequent cooling. In addition, the additive liquid lowers the concentration of any high volatility fluorine compounds in the condensed phase, resulting in a reduction in their concentrations in the equilibrium vapor phase which is separated and passed out of the system without being subject to recovery. The additive liquid has an atmospheric pressure freezing point lower than 100° K. and a vapor pressure less than 1.0 mmHg, preferably less than 0.01 mmHg at 100° K. Perfluoropropane ($C_3F_8$) is the preferred additive liquid. Propane, ethane and mixtures thereof may also be used as the additive liquid.

Mixed stream 102 is then passed through at least one heat exchanger wherein it is cooled to a temperature within the range of from 90° to 130° K. such that the feed is partially condensed to produce vapor comprising carrier gas and additive liquid comprising fluorine compounds. In the embodiment illustrated in FIG. 2, mixed stream 102 passes through two such heat exchangers 103 and 104.

Resulting stream 105 is then passed to phase separator 106 where it is separated into nitrogen-containing vapor and additive liquid comprising fluorine compounds. The nitrogen-containing vapor is passed as stream 107 through heat exchangers 104 and 103 to carry out, by indirect heat exchange, the partial condensation of feed stream 102, and the resulting warmed nitrogen-containing vapor is removed from the system as stream 108.

In the embodiment illustrated in FIG. 2, additional cryogenic liquid, e.g. liquid nitrogen, is used to carry out by indirect heat exchange the partial condensation of the feed. In this embodiment illustrated in FIG. 2, cryogenic liquid is passed from within tank 116 in line 109 through heat exchanger 104. Resulting stream 110 is then combined with stream 113 to form stream 111 which is passed through valve 112 into line 107 upstream of heat exchanger 103. Boil off vapor from tank 116 is passed out from tank 116 in stream 113.

Fluorine compound-containing additive liquid is withdrawn from phase separator 106 as stream 119 and preferably passed through valve 120 into batch storage tank 121 where it is stored for subsequent batch-wise processing. The use of tank 121 is advantageous when there is a significant variance in the fluorine compound concentration in the gaseous feed and/or in the gaseous feed flow rate. Fluorine compound-containing additive liquid is passed from tank 121 in stream 124 through valve 125 as column feed into the lower portion of rectification column 126 which is driven by external heat input through heat input line 127.

The rectification step may be operated in a batch mode. Within rectification column 126 the column feed is separated by cryogenic rectification into fluorine compound-containing top vapor and bottom additive liquid.

Top vapor comprising fluorine compounds is withdrawn from the upper portion of rectification column 126 as stream 128 and at least a portion thereof is recovered as product fluorine compounds. In the embodiment illustrated in FIG. 2, stream 128 is passed through tank 116 in indirect heat exchange with the liquid within tank 116 and is partially condensed. A portion 129 of stream 128 may be passed through valve 130 so as to bypass tank 116. Resulting partially condensed stream 131 is then passed into phase separator 132. Vapor, comprised primarily of carrier gas, is passed out from phase separator 132 in stream 133 and into stream 107. Liquid is withdrawn from phase separator 132 as stream 135. A portion 136 of stream 135 is passed through valve 137 and into the upper portion of rectification column 126 as reflux. After essentially all of the carrier gas has been exhausted from rectification column 126 through stream 128, another portion 138 of stream 135 is passed through valve 139 and recovered as product fluorine compounds.

Bottom additive liquid is withdrawn from the lower portion of rectification column 126 as stream 142 and passed through valve 143 into additive liquid storage tank 144. Any liquid that is vaporized within tank 144 may be passed out from tank 144 through valve 145 in line 146 and combined with column feed stream 124 and then into rectification column 126. From tank 144 the bottom additive liquid is withdrawn as stream 147 and combined with gaseous feed stream 101 to form mixed stream 102.

Figure 3:
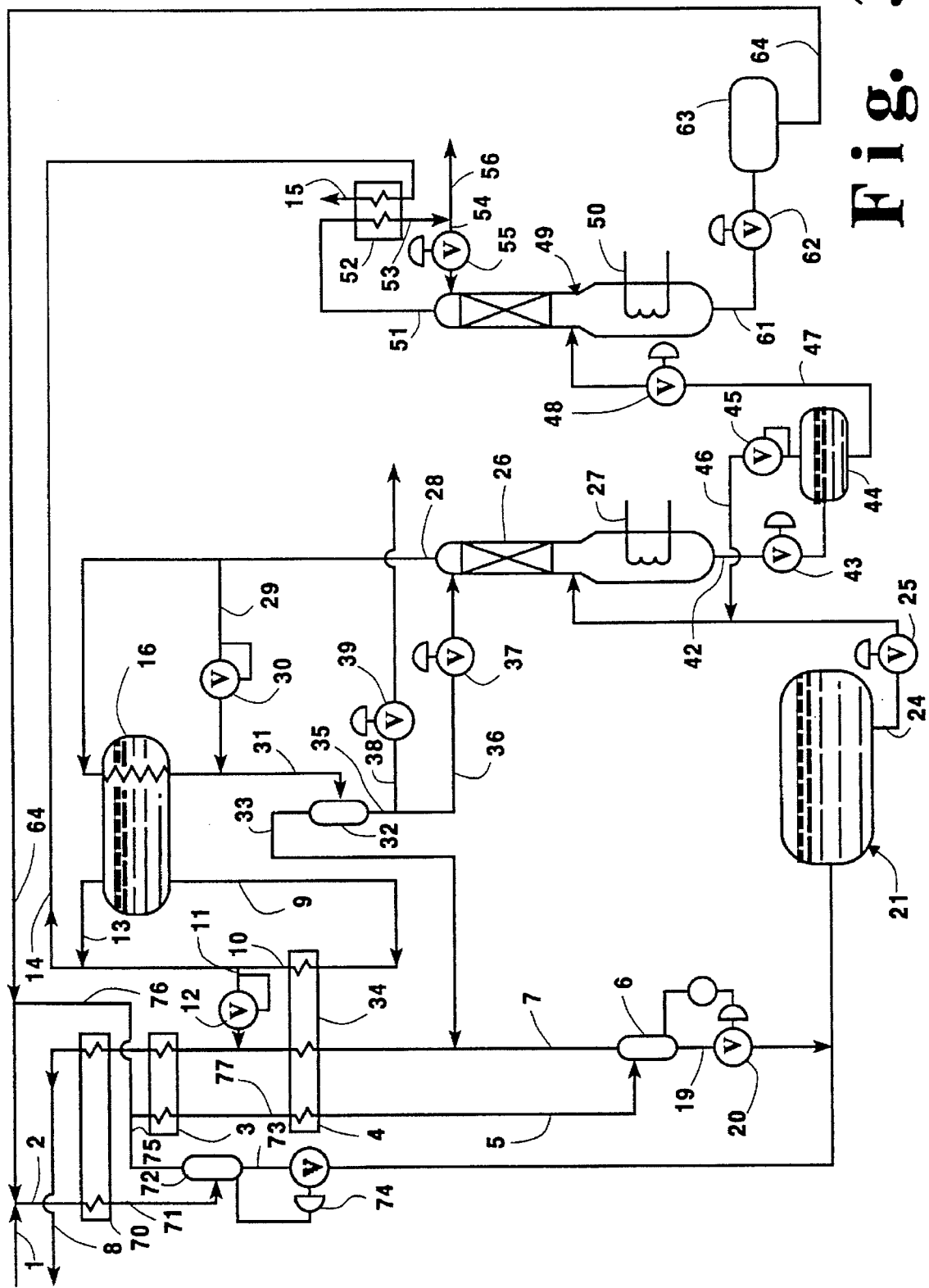
FIG. 3 is a schematic flow diagram of another embodiment of the fluorine compound recovery system of this invention wherein the partial condensation of the feed is carried out in more than one stage.

FIG. 3 illustrates the use of staged partial condensation of the feed. The embodiment illustrated in FIG. 3 is a two column embodiment similar to that illustrated in FIG. 1. The numerals in FIG. 3 are the same as those of FIG. 1 for the common elements and these common elements will not be discussed again in detail.

Referring now to FIG. 3, mixed stream 2 is passed through heat exchanger 70 wherein it is cooled and partially condensed. Resulting stream 71 is passed from heat exchanger 70 into phase separator 72 wherein it is separated into vapor enriched in carrier gas and liquid enriched in fluorine compounds. The liquid is passed out from phase separator 72 in stream 73, through valve 74 and into tank 21 for further processing as previously described. Vapor is passed out of phase separator 72 in stream 75 and combined with additive liquid in stream 76 to form staged mixed stream 77 which is then partially condensed by passage through heat exchangers 3 and 4 to form stream 5 which is further processed as previously described. Vapor stream 7 additionally passes through heat exchanger 70 to carry out by indirect heat exchange the initial partial condensation of feed stream 2.

Now by the use of the cryogenic fluorine compound recovery system of this invention one can effectively and efficiently recover fluorine compounds from a carrier gas stream, such as an effluent stream from a semiconductor production facility, without generating significant amounts of waste gas or requiring significant further separation to produce fluorine compound products suitable for use. Furthermore, the invention enables one to effectively handle a feed gas stream which has a highly variable flow rate and/or fluorine compound concentration.

Although the invention has been described in detail with reference to certain embodiments, those skilled in the art will recognize that there are other embodiments of the invention within the spirit and the scope of the claims.

We claim:

1. A method for recovering fluorine compounds comprising:

(A) combining a gaseous feed comprising carrier gas, high volatility fluorine compounds and low volatility fluorine compounds with additive liquid to form a mixed stream;

(B) partially condensing the mixed stream to produce vapor comprising carrier gas and additive liquid comprising high volatility and low volatility fluorine compounds;

(C) passing the additive liquid comprising high volatility and low volatility fluorine compounds into a first rectification column as first column feed and separating the first column feed within said first rectification column by cryogenic rectification into top vapor comprising high volatility fluorine compounds and additive liquid comprising low volatility fluorine compounds;

(D) withdrawing top vapor comprising high volatility fluorine compounds from the first rectification column and recovering at least a portion thereof as product fluorine compounds;

(E) passing additive liquid comprising low volatility fluorine compounds into a second rectification column as second column feed and separating the second column feed within said second rectification column by cryogenic rectification into top vapor comprising low volatility fluorine compounds and residual additive liquid; and (F) withdrawing top vapor comprising low volatility fluorine compounds from the second rectification column and recovering at least a portion thereof as product fluorine compounds.

2. The method of claim 1 wherein the gaseous feed is partially condensed by indirect heat exchange with the vapor comprising carrier gas.

3. The method of claim 1 wherein the gaseous feed is partially condensed by indirect heat exchange with vapor taken from the upper portion of the first rectification column.

4. The method of claim 1 wherein the partial condensation of the gaseous feed is carried out in more than one stage.

5. The method of claim 1 wherein residual additive liquid is withdrawn from the second rectification column and combined with the gaseous feed to form the mixed stream.

6. The method of claim 1 wherein the additive liquid comprises perfluoropropane.

7. Apparatus for the recovery of fluorine compounds comprising:

(A) means for combining additive liquid with gaseous feed comprising fluorine compounds to produce a mixed stream;

(B) a heat exchanger and means for passing the mixed stream through the heat exchanger;

(C) a first rectification column and means for passing liquid from the heat exchanger into the first rectification column;

(D) means for recovering fluorine compounds taken from the upper portion of the first rectification column;

(E) a second rectification column and means for passing liquid from the lower portion of the first rectification column into the second rectification column; and (F) means for recovering fluorine compounds taken from the upper portion of the second rectification column.

8. The apparatus of claim 7 further comprising means for passing fluid taken from the upper portion of the first rectification column through the heat exchanger.

9. The apparatus of claim 7 wherein the means for passing liquid from the heat exchanger into the first rectification column comprises a batch storage tank.

10. The apparatus of claim 7 wherein the means for passing liquid from the lower portion of the first rectification column into the second rectification column comprises a batch storage tank.

11. The apparatus of claim 7 wherein the means for combining additive liquid with gaseous feed comprises means for passing liquid from the lower portion of the second rectification column.

12. A method for recovering fluorine compounds comprising:

(A) combining a gaseous feed comprising carrier gas and fluorine compounds with additive liquid to form a mixed stream;

(B) partially condensing the mixed stream to produce vapor comprising carrier gas and fluorine compound-containing additive liquid;

(C) passing the fluorine compound-containing additive liquid into a rectification column as column feed and separating the column feed within said rectification column by cryogenic rectification into fluorine compound-containing top vapor and bottom additive liquid; and (D) withdrawing fluorine compound-containing top vapor from the rectification column and recovering at least a portion thereof as product fluorine compounds.

13. The method of claim 12 wherein the gaseous feed is partially condensed by indirect heat exchange with the vapor comprising carrier gas.

14. The method of claim 12 wherein the gaseous feed is partially condensed by indirect heat exchange with vapor taken from the upper portion of the rectification column.

15. The method of claim 12 wherein bottom additive liquid is withdrawn from the rectification column and combined with the gaseous feed to form the mixed stream.

16. The method of claim 12 wherein the additive liquid comprises perfluoropropane.

17. Apparatus for the recovery of fluorine compounds comprising:

(A) means for combining additive liquid with gaseous feed comprising fluorine compounds to produce a mixed stream;

(B) a heat exchanger and means for passing the mixed stream through the heat exchanger;

(C) a rectification column and means for passing liquid from the heat exchanger into the rectification column; and (D) means for recovering fluorine compounds taken from the upper portion of the rectification column.

18. The apparatus of claim 17 further comprising means for passing fluid taken from the upper portion of the rectification column through the heat exchanger.

19. The apparatus of claim 17 wherein the means for passing liquid from the heat exchanger into the rectification column comprises a batch storage tank.

20. The apparatus of claim 17 wherein the means for combining additive liquid with gaseous feed comprises means for passing liquid from the lower portion of the rectification column.

* * * * *